US012758193B2

(12) United States Patent
Usumura et al.

(10) Patent No.: US 12,758,193 B2
(45) Date of Patent: Oct. 13, 2026

(54) MEDICAL INFORMATION PROCESSING DEVICE, ULTRASONIC DIAGNOSIS DEVICE, AND MEDICAL INFORMATION PROCESSING METHOD

(71) Applicant: Canon Kabushiki Kaisha, Tokyo (JP)

(72) Inventors: Masashi Usumura, Nasushiobara (JP); Hiroki Takahashi, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 18/900,153

(22) Filed: Sep. 27, 2024

(65) Prior Publication Data

US 2025/0143675 A1 May 8, 2025

(30) Foreign Application Priority Data

Sep. 27, 2023 (JP) ................................ 2023-164256
Dec. 18, 2023 (JP) ................................ 2023-213404
Dec. 18, 2023 (JP) ................................ 2023-213405
Dec. 18, 2023 (JP) ................................ 2023-213406
Sep. 25, 2024 (JP) ................................ 2024-166274

(51) Int. Cl.
*A61B 8/00* (2006.01)
*A61B 8/06* (2006.01)

(52) U.S. Cl.
CPC .............. *A61B 8/5215* (2013.01); *A61B 8/06* (2013.01); *A61B 8/481* (2013.01)

(58) Field of Classification Search
CPC .......... A61B 8/06; A61B 8/481; A61B 8/5215
See application file for complete search history.

(56) References Cited

U.S. PATENT DOCUMENTS

2021/0104080 A1* 4/2021 Maltz ...................... G06F 30/27
2022/0117494 A1* 4/2022 Huang ................. A61B 5/0095
2023/0240645 A1* 8/2023 Sadeghi ............... A61B 8/0883
600/437
2023/0243944 A1* 8/2023 Srinivasan .......... G01S 7/52003
367/7
2025/0143674 A1* 5/2025 Usumura ............ A61B 8/5223

OTHER PUBLICATIONS

Jorgen Arendt Jensen, et al., Fast super resolution ultrasound imaging using the erythrocytes, Proc. SPIE 12038, Medical Imaging 2022: Ultrasonic Imaging and Tomography, 120380E, Apr. 4, 2022, 8 pages.

* cited by examiner

*Primary Examiner* — Dixomara Vargas
(74) *Attorney, Agent, or Firm* — Oblon, McClelland, Maier & Neustadt, L.L.P.

(57) ABSTRACT

A medical information processing device according to an embodiment includes a processing circuit. The processing circuit acquires first ultrasonic data obtained based on a result of an ultrasonic scan of a subject, continuously extracts signal components representing an object from the first ultrasonic data, and outputs second ultrasonic data, based on the continuously extracted signal components representing the object.

16 Claims, 17 Drawing Sheets

| | | | | | | | | | |
|---|---|---|---|---|---|---|---|---|---|
| 0 | 0 | 1 | 2 | 3 | 5 | 7 | 6 | 5 | 3 |
| 4 | 6 | 7 | 5 | 9 | 8 | 8 | 4 | 5 | 3 |
| 3 | 4 | 5 | 8 | 5 | 7 | 9 | 8 | 3 | 2 |
| 2 | 6 | 4 | 8 | 3 | 4 | 9 | 9 | 7 | 3 |
| 1 | 5 | 3 | 9 | 5 | 4 | 7 | 8 | 8 | 1 |
| 3 | 4 | 7 | 8 | 4 | 5 | 8 | 9 | 8 | 0 |
| 2 | 2 | 8 | 9 | 4 | 6 | 9 | 1 | 2 | 1 |
| 1 | 3 | 5 | 8 | 8 | 9 | 7 | 9 | 3 | 1 |
| 0 | 4 | 3 | 7 | 6 | 7 | 8 | 2 | 2 | 0 |
| 1 | 2 | 3 | 3 | 5 | 1 | 3 | 2 | 1 | 1 |

| | | | | | | | | | |
|---|---|---|---|---|---|---|---|---|---|
| 0 | 0 | 1 | 2 | 3 | 5 | 7 | 6 | 5 | 3 |
| 4 | 6 | 7 | 5 | 9 | 8 | 8 | 4 | 5 | 3 |
| 3 | 4 | 5 | 8 | 5 | 7 | 9 | 8 | 3 | 2 |
| 2 | 6 | 4 | 8 | 3 | 4 | 9 | 9 | 7 | 3 |
| 1 | 5 | 3 | 9 | 5 | 4 | 7 | 8 | 8 | 1 |
| 3 | 4 | 7 | 8 | 4 | 5 | 8 | 9 | 8 | 0 |
| 2 | 2 | 8 | 9 | 4 | 6 | 9 | 1 | 2 | 1 |
| 1 | 3 | 5 | 8 | 8 | 9 | 7 | 9 | 3 | 1 |
| 0 | 4 | 3 | 7 | 6 | 7 | 8 | 2 | 2 | 0 |
| 1 | 2 | 3 | 3 | 5 | 1 | 3 | 2 | 1 | 1 |

| | | | | | | | | | |
|---|---|---|---|---|---|---|---|---|---|
| 0 | 0 | 1 | 2 | 3 | 5 | 7 | 6 | 5 | 3 |
| 4 | 6 | 7 | 5 | 9 | 8 | 8 | 4 | 5 | 3 |
| 3 | 4 | 5 | 8 | 5 | 7 | 9 | 8 | 3 | 2 |
| 2 | 6 | 4 | 8 | 3 | 4 | 9 | 9 | 7 | 3 |
| 1 | 5 | 3 | 9 | 5 | 4 | 7 | 8 | 8 | 1 |
| 3 | 4 | 7 | 8 | 4 | 5 | 8 | 9 | 8 | 0 |
| 2 | 2 | 8 | 9 | 4 | 6 | 9 | 1 | 2 | 1 |
| 1 | 3 | 5 | 8 | 8 | 9 | 7 | 9 | 3 | 1 |
| 0 | 4 | 3 | 7 | 6 | 7 | 8 | 2 | 2 | 0 |
| 1 | 2 | 3 | 3 | 5 | 1 | 3 | 2 | 1 | 1 |

MEDICAL INFORMATION PROCESSING DEVICE, ULTRASONIC DIAGNOSIS DEVICE, AND MEDICAL INFORMATION PROCESSING METHOD

CROSS-REFERENCE TO RELATED APPLICATIONS

This application is based upon and claims the benefit of priority from Japanese Patent Application No. 2023-213405, filed on Dec. 18, 2023; Japanese Patent Application No. 2023-164256, filed on Sep. 27, 2023; Japanese Patent Application No. 2023-213404, filed on Dec. 18, 2023; Japanese Patent Application No. 2023-213406, filed on Dec. 18, 2023; and Japanese Patent Application No. 2024-166274, filed on Sep. 25, 2024, the entire contents of all of which are incorporated herein by reference.

FIELD

Embodiments disclosed in the present specification and drawings relate generally to a medical information processing device, an ultrasonic diagnosis device, and a medical information processing method.

BACKGROUND

Ultrasonic diagnosis devices are widely used to observe and diagnose blood flow in the body. The ultrasonic diagnosis device generates and displays blood flow information from reflected ultrasonic waves using a Doppler method based on a Doppler effect. The blood flow information generated and displayed by the ultrasonic diagnosis device includes color Doppler images, Doppler waveforms (Doppler spectrum), and the like.

The color Doppler images are captured by a color flow mapping (CFM) method. In the CFM method, ultrasonic waves are transmitted and received a plurality of times on a plurality of scanning lines. Then, by applying a moving target indicator (MTI) filter to data sequences at the same position, signals derived from stationary or slowly moving tissue (clutter signals) are suppressed and signals derived from the blood flow are extracted. In the CFM method, the blood flow information such as a velocity value, a variance value, and a power value of the blood flow is estimated from these blood flow signals, and the distribution of the estimated results is displayed as a Doppler image.

It is known that the resolution in B-mode data and Doppler data decreases by the point spread function (PSF), which is determined by the wavelength of the transmission ultrasonic waves and the transmission/reception aperture width. There are solutions such as increasing the frequency of the transmission ultrasonic waves, but since there is a limitation in the frequency bandwidth of a probe, the resolution of the images that can be acquired is limited.

According to "Fast super resolution ultrasonic imaging using the erythrocytes" by Jorgen Arendt Jensen et al., Proc. SPIE 12038, Medical Imaging 2022: Ultrasonic Imaging and Tomography, 120380E, Apr. 4, 2022, blood flow data with improved resolution is generated by extracting and integrating the portions with high signal values (amplitude values) from a plurality of pieces of blood flow data that are continuous in a time direction. More specifically, "Fast super resolution ultrasonic imaging using the erythrocytes" describes the use of the fact that the amplitude distribution characteristic of a speckle pattern in blood flow data can be substantially approximated by a probability distribution called the Rayleigh distribution. In this way, a high-luminance, spatially sparse signal with a small probability of occurrence but a large signal value (amplitude value) is extracted from each piece of blood flow data and the obtained signals are integrated.

However, in the method described in "Fast super resolution ultrasonic imaging using the erythrocytes", if the number of frames used to extract an object is small, the object is extracted discretely (discontinuously) and high-resolution blood flow data (ultrasonic data) cannot be obtained. On the other hand, if a large number of frames are used, the load on the arithmetic processing increases, resulting in poor responsiveness.

DETAILED DESCRIPTION

Figure 1:
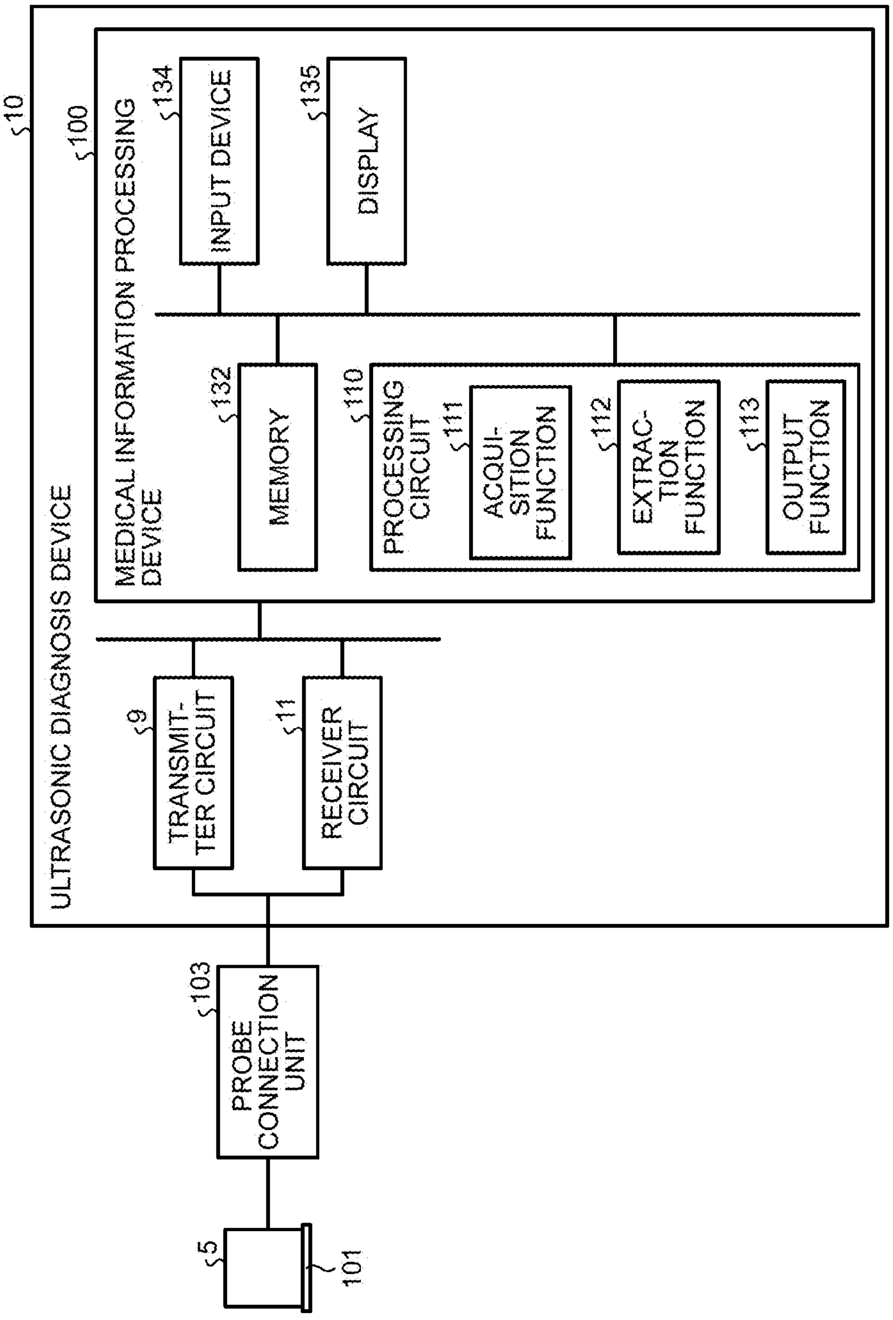
FIG. 1 is a block diagram illustrating a structure of an ultrasonic diagnosis device according to an embodiment.

A medical information processing device provided in one aspect of the present invention includes a processing circuit. The processing circuit acquires first ultrasonic data obtained based on a result of an ultrasonic scan of a subject, continuously extracts signal components representing an object from the first ultrasonic data, and outputs second ultrasonic data, based on the continuously extracted signal components representing the object.

First Embodiment

One embodiment of a medical information processing device, an ultrasonic diagnosis device, and a medical information processing method is described below in detail with reference to the drawings.

The ultrasonic diagnosis device according to this embodiment causes an ultrasonic probe to perform an ultrasonic scan and collects a plurality of pieces of frame data that are obtained by the ultrasonic scan and that are continuous in a time direction (a plurality of pieces of frame data within a predetermined time). The frame data is collected at a predetermined frame rate by performing the ultrasonic scan. The frame data refers to any of reception data, measurement data, blood flow data, and tissue data. The reception data is, for example, a reception signal of ultrasonic waves received by the ultrasonic probe (for example, CH data). The measurement data is data (for example, IQ data) obtained by performing delay and sum and quadrature detection processing on the reception signal of the ultrasonic waves. The blood flow data is data (for example, power signal data) where the information of the measurement data that is derived from the blood flow is extracted or emphasized. The tissue data is data (for example, B-mode data) where the information that is derived from the tissue is extracted or emphasized.

The measurement data includes, for example, tissue-derived information (tissue signal component (clutter)) and blood flow-derived information (blood flow signal component). The blood flow-derived information may include not just information derived from blood, but also information derived from a contract agent in the blood. The blood flow data is data where the blood flow-derived information is extracted or emphasized, and includes the velocity value, the variance value, and the power value of the blood flow.

The extraction of the blood flow-derived information corresponds to, for example, an operation of extracting the blood flow signal component from the measurement data. The emphasis of the blood flow-derived information corresponds to, for example, an operation of making the blood flow signal component stand out relative to the tissue signal component. The blood flow data may be obtained by a process of extracting or emphasizing the blood flow-derived information, or by a process of removing or reducing the tissue-derived information.

The ultrasonic diagnosis device acquires addition data obtained by adding up the pieces of frame data, as first ultrasonic data. The first ultrasonic data, for example, has a higher signal-noise (SN) ratio than each piece of frame data. The ultrasonic diagnosis device performs a process of continuously extracting the signal components representing the object from the first ultrasonic data. The object includes, for example, any of blood, an in-body tissue, and a contract agent.

The ultrasonic diagnosis device outputs second ultrasonic data on the basis of the continuously extracted signal components representing the object. The second ultrasonic data may be any of synthesis data obtained by synthesizing the continuously extracted signal components representing the object and the first ultrasonic data, correction data obtained by correcting the first ultrasonic data, based on the continuously extracted signal components representing the object, and data including the continuously extracted signal components representing the object.

By this ultrasonic diagnosis device according to this embodiment, the object can be extracted continuously even if the number of frames used to extract the object is small. Thus, highly responsive and high-resolution ultrasonic data (high-resolution data) can be obtained. Moreover, by the ultrasonic diagnosis device according to this embodiment, the process of extracting the signal components representing the object can be reduced to 1/frame number, which can significantly reduce the arithmetic load compared to the conventional device.

Although the example of applying the present disclosure to the ultrasonic diagnosis device has been described so far, the present disclosure may be applied to modalities (medical information processing devices) other than the ultrasonic diagnosis device. For example, the present disclosure can be applied to medical information processing devices such as workstations and servers that acquire ultrasonic data obtained based on the results of ultrasonic scans of subjects.

FIG. 1 is a block diagram illustrating a structure of the ultrasonic diagnosis device according to the embodiment. An ultrasonic diagnosis device 10 is a device that generates ultrasonic data on the basis of reception signals (reflection wave signals) received from an ultrasonic probe 5. The ultrasonic diagnosis device 10 illustrated in FIG. 1 can generate two-dimensional ultrasonic data on the basis of two-dimensional reception signals and generate three-dimensional ultrasonic data on the basis of three-dimensional reception signals. However, the embodiment is applicable even when the ultrasonic diagnosis device 10 is a device dedicated to the two-dimensional data. The ultrasonic diagnosis device 10 includes a transmitter circuit 9, a receiver circuit 11, and a medical information processing device 100.

The ultrasonic probe 5 is, for example, an electronic scanning-type probe and has a plurality of transducer elements 101 arranged one-dimensionally or two-dimensionally at its tip. The transducer element 101 is a piezoelectric element (electromechanical conversion element) that performs mutual conversion between electrical signals (voltage pulse signals) and ultrasonic waves (acoustic waves). The ultrasonic probe 5 transmits ultrasonic waves from the transducer elements 101 to the subject, and receives the reflection ultrasonic waves from the subject by the transducer elements 101. The reflection acoustic waves reflect differences in acoustic impedance within the subject. When the transmitted ultrasonic pulse is reflected on a moving blood flow or on a surface of a heart wall or the like, the reflection ultrasonic waves are subject to frequency shift depending on a velocity signal component relative to an ultrasonic wave transmission direction of a moving object due to the Doppler effect.

A probe connection unit 103 connects the ultrasonic probe 5 and transmits and receives ultrasonic waves to and from the ultrasonic probe 5. The connection of the ultrasonic probe 5 by the probe connection unit 103 may or may not use a wire. In the case of using the wire, the probe connection unit 5 includes a connector part (receptacle) to which a connector (plug) of the ultrasonic probe 5 is connected. In the case of not using the wire, a communication unit that performs wireless communication with the ultrasonic probe 5 is provided.

The transmitter circuit 9 is a transmitter unit that outputs pulse signals (driving signals) to the transducer elements 101. By applying the pulse signals with time differences to the transducer elements 101, ultrasonic waves with different delay times are transmitted from the transducer elements 101 to form a transmission ultrasonic beam. The direction and focus of the transmission ultrasonic beam can be controlled by selectively changing the transducer element 101 to which the pulse signal is applied (i.e., the transducer element 101 to be driven) or by changing the delay time (application timing) of the pulse signal. By sequentially changing the direction and focus of the transmission ultrasonic beam, an observation region inside the subject is scanned. By changing the delay time of the pulse signal, a transmission ultrasonic beam may be formed that is a plane wave (a focus is far away) or a diffuse wave (a focus point is the opposite of the ultrasonic transmission direction with respect to the transducer elements 101). Alternatively, one transducer element or some of the transducer elements 101 may be used to form the transmission ultrasonic beam. The transmitter circuit 9 transmits a pulse signal with a predetermined driving waveform to the transducer element 101 to generate the transmission ultrasonic wave with a predetermined transmission waveform at the transducer element 101.

The receiver circuit 11 is a reception unit that inputs the electrical signal output from the transducer element 101, which has received the reflection ultrasonic wave, as the reception signal. The reception signal is input to a processing circuit 110. In this embodiment, both an analog signal output from the transducer element 101 and digital data sampled (digitally converted) from the analog signal are referred to as the reception signal without any particular distinction. However, depending on the context, the reception signal may be described as reception data or measurement data for the purpose of explicitly indicating that the data is digital data.

The medical information processing device 100 is connected to the transmitter circuit 9 and the receiver circuit 11, processes signals received from the receiver circuit 11, and executes control of the transmitter circuit 9. The medical information processing device 100 includes the processing circuit 110, a memory 132, an input device 134, and a display 135.

The memory 132 includes a semiconductor memory element such as a random-access memory (RAM) or a flash memory, a hard disk, an optical disc, or the like. The memory 132 is a memory that stores therein data such as image data for display generated by the processing circuit 110. The memory 132 can also store therein the reception signal (reflection wave signal) output by the receiver circuit 11. In addition, the memory 132 stores therein control programs for performing ultrasonic transmission and reception, image processing, and display processing, as well as diagnostic information (for example, patient ID, physician's findings, etc.), diagnostic protocols, various body marks, and other data as needed.

The input device 134 receives various instructions and information input from an operator. The input device 134 includes an input interface device such as a mouse, a keyboard, buttons, or a trackball.

The display 135 displays a graphical user interface (GUI) for receiving the input of imaging conditions and various images under the control of the processing circuit 110. The display 135 includes, for example, a display interface device such as a liquid crystal display.

The processing circuit 110 controls each part of the ultrasonic diagnosis device 10, thereby controlling the entire ultrasonic diagnosis device 10. In FIG. 1, the processing circuit 110 is described as being realized alone, but the processing circuit 110 may alternatively be realized by combining a number of independent processors. Alternatively, specific functions may be formed of dedicated independent circuits, such as an application specific integrated circuit (ASIC).

The term "processor" used in the above description means, for example, a circuit such as a central processing unit (CPU), a graphical processing unit (GPU), an application specific integrated circuit (ASIC), a programmable logic device (for example, simple programmable logic device (SPLD)), a complex programmable logic device (CPLD), or a field programmable gate array (FPGA). The processor reads out and executes a computer program saved in the memory 132 to realize the function.

The processing circuit 110 causes the ultrasonic probe 5 to perform an ultrasonic scan and collects a plurality of pieces of frame data that are obtained by the ultrasonic scan and that are continuous in the time direction (a plurality of pieces of frame data within a predetermined time). The processing circuit 110 performs delay and sum and quadrature detection processing on the reception signal (CH data) collected through the receiver circuit 11. The delay and sum processing is a process of adding up the reception signals of the transducer elements 101 with the delay time and weight varied for each transducer element 101, and is also known as delay and sum (DAS) beam forming. The quadrature detection processing is a process of converting the reception signal into an in-phase signal and a quadrature signal (IQ data (measurement data)) in a baseband range. In addition, the reception signal may be subjected to a process using adaptive beam forming, model-based processing, machine learning, or the like.

The processing circuit 110 may also estimate the amount of tissue displacement due to body motion of the subject or the like between the pieces of frame data, and correct each piece of frame data on the basis of the results of estimation. Specifically, the processing circuit 110 calculates the amount of tissue displacement due to body motion or the like between the frames from the pieces of frame data. The processing circuit 110 corrects the frame data on the basis of the calculated amount of displacement.

Moreover, the processing circuit 110 performs an envelope detection process, a logarithmic compression process, or the like so as to generate B-mode data (data in which tissue-derived information is extracted or emphasized) representing, in luminance, the signal intensity at each point in the observation region. The processing circuit 110 also generates blood flow data (power signal data) in which the blood flow-derived information is extracted or emphasized in the measurement data.

For example, the processing circuit 110 applies a moving target indicator (MTI) filter to the pieces of frame data. This reduces the information derived from tissue that is stationary or has little movement between the frames (tissue signal components (clutter)), and extracts the blood flow-derived information (blood flow signal components). As the MTI filter, a filter with a fixed filter coefficient, such as a Butterworth-type infinite impulse response (IIR) filter or a polynomial regression filter may be used. The MTI filter may be an adaptive filter that varies its coefficient according to the input signal using eigenvalue or singular value decomposition, or the like.

The processing circuit 110 may also decompose the frame data into a plurality of bases by eigenvalue or singular value decomposition, or the like, remove the tissue-derived information by extracting a specific base, and extract the blood flow-derived information. The processing circuit 110 may cause a Doppler processing function **110*i*** to obtain a velocity vector for each set of coordinates in the reception signal data and obtain a blood flow vector representing the size and direction of the blood flow in accordance with a vector Doppler method, a speckle tracking method, a vector flow mapping method, or the like. In addition to the methods given here, any method that can extract or emphasize the blood flow-derived information included in the frame data (reception data and measurement data) or remove or reduce the tissue-derived information may be used.

Figure 4:
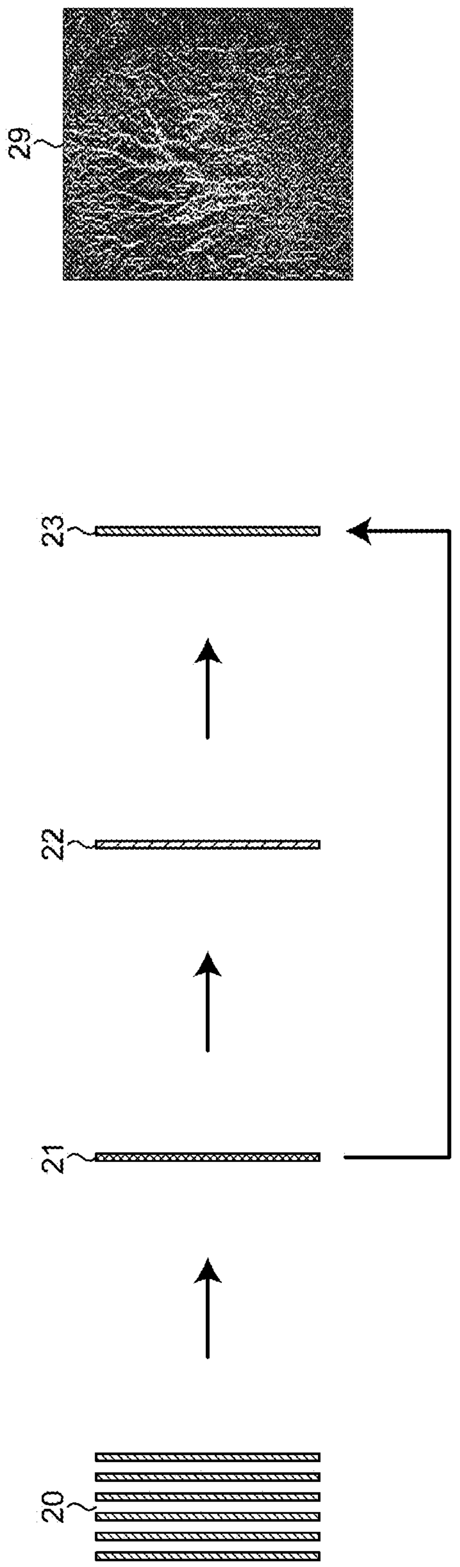
FIG. 4 is a schematic diagram for describing a process to be performed by the medical information processing device according to the embodiment.

Furthermore, the processing circuit 110 reads out and executes a computer program stored in the memory 132 so as to activate an acquisition function 111, an extraction function 112, and an output function 113, thereby outputting high-resolution ultrasonic data (high-resolution image data 29 illustrated in FIG. 4).

Before the process of outputting the high-resolution ultrasonic data using the ultrasonic diagnosis device 10 configured as above is described, a method of generating high-resolution data according to conventional art (for example, the method described in "Fast super resolution ultrasonic imaging using the erythrocytes") is described.

Figure 2:
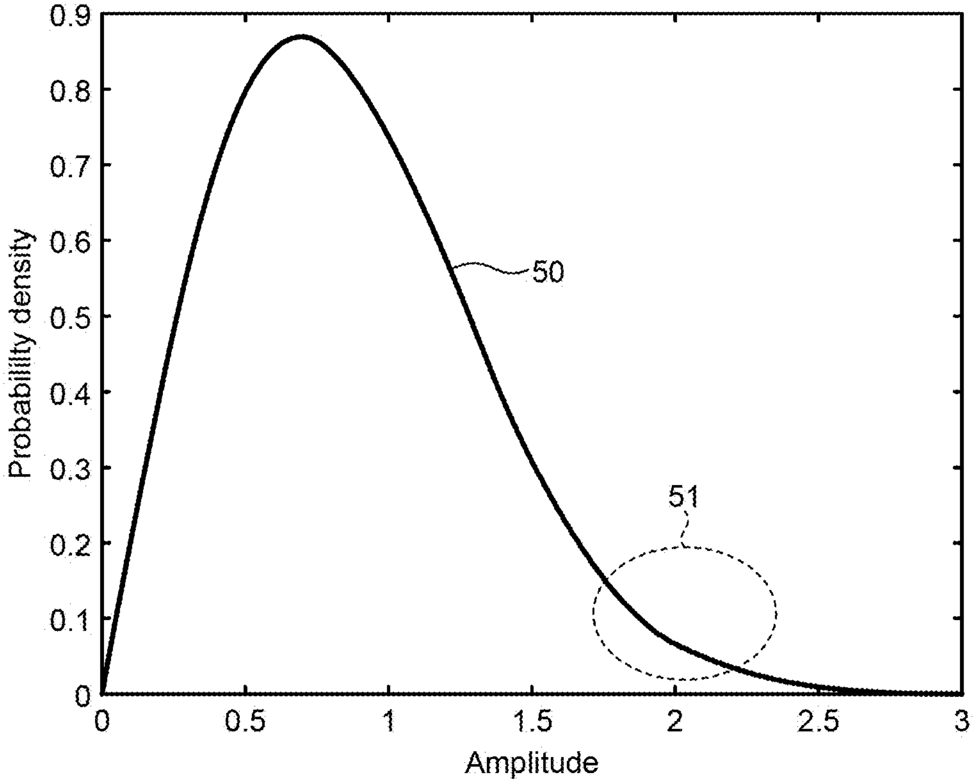
FIG. 2 is a diagram for describing a Rayleigh distribution.
Figure 5:
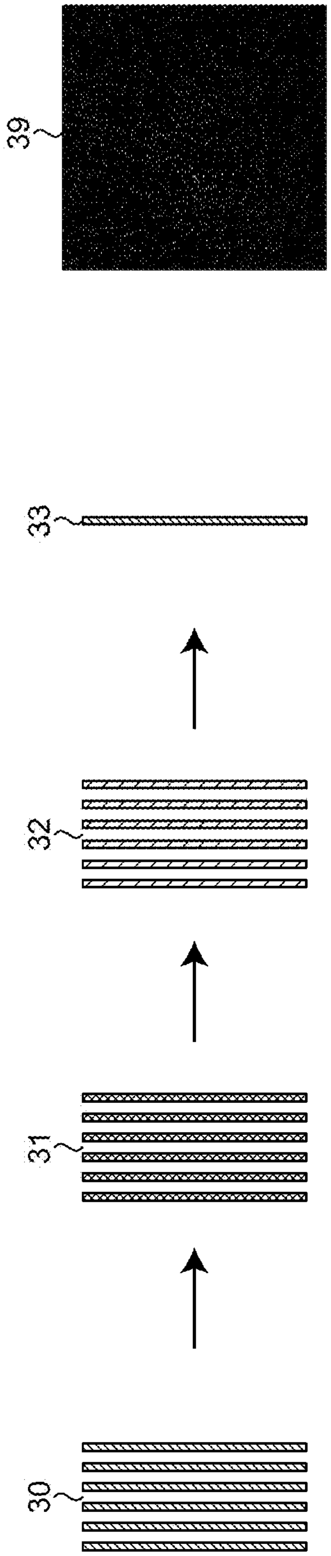
FIG. 5 is a schematic diagram for describing a process according to a comparative example.

It is known that an amplitude distribution characteristic 50 of a speckle pattern of the blood flow data can be substantially approximated by a probability distribution called the Rayleigh distribution, as illustrated in FIG. 2. In the method of generating the high-resolution data in the conventional art, as illustrated in FIG. 5, a high-luminance, spatially sparse signal 32 (area 51 indicated in FIG. 2) with a small probability of occurrence but a large signal value (amplitude value) is extracted from a plurality of pieces of blood flow data 31 corresponding to respective pieces of frame data 30 and by integrating this, ultrasonic data 33 (ultrasonic image 39) is generated.

However, the number of frames required to generate a single piece of high-resolution blood flow data (ultrasonic data 33 illustrated in FIG. 5) by this method is about several thousand to several tens of thousands. In this method, if the number of frames used to extract the object is small, the object is extracted discretely (discontinuously) and the high-resolution blood flow data cannot be obtained. On the other hand, using more frames increases the load on the arithmetic processing, resulting in poor responsiveness.

Figure 3:
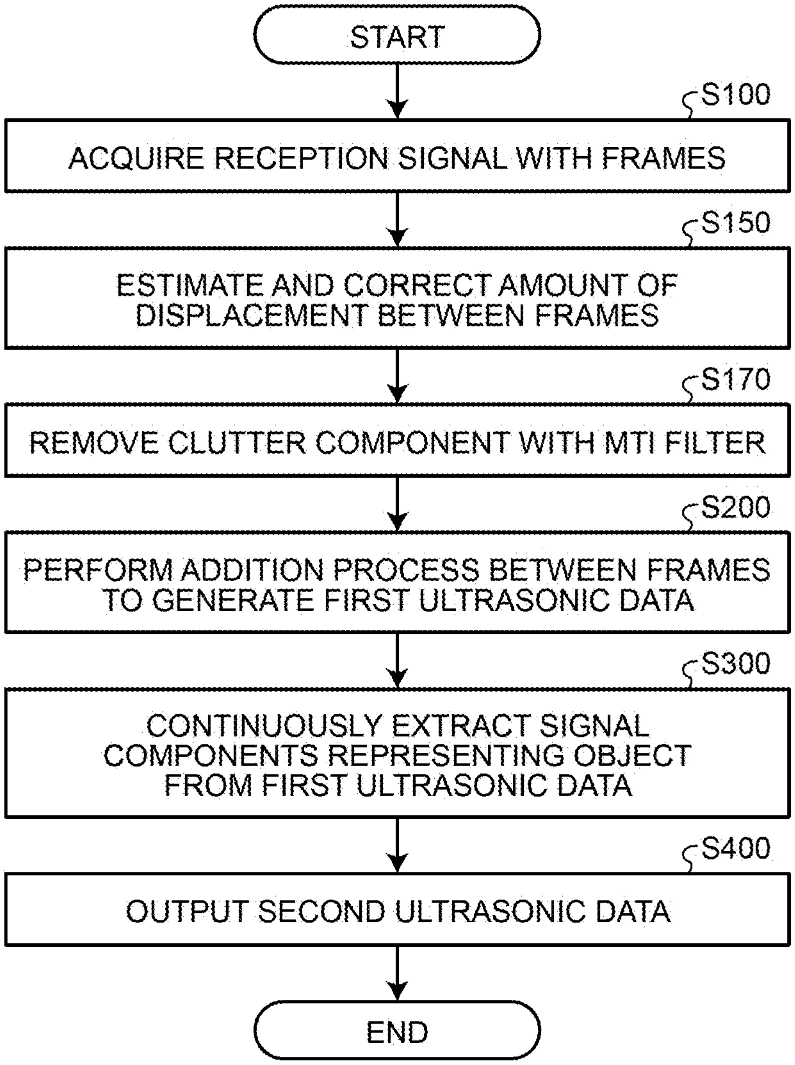
FIG. 3 is a flowchart expressing a procedure of a process to be performed by a medical information processing device illustrated in FIG. 1.

With reference to FIG. 3 and FIG. 4, the process to be performed by the medical information processing device 100 will be described below. The processing circuit 110 causes the acquisition function 111 to collect and acquire a plurality of pieces of frame data 20 (reception signals, measurement data, etc.) that are obtained by the ultrasonic scan and that are continuous in the time direction as illustrated in FIG. 4 (step S100). The number of frames in the frame data 20 when generating the high-resolution data is about the same as that when generating the general Doppler data. For example, the number of frames (packets) used to generate the Doppler data is about several dozen. On the other hand, the number of pieces of frame data 20 to be collected by the acquisition function 111 is about several dozen to several hundred, which is much smaller than the number of pieces of frame data to be collected by the method according to the conventional art (about several thousand to several tens of thousands).

The processing circuit 110 estimates the amount of tissue displacement due to body motion of the subject or the like between the pieces of frame data, and corrects each piece of frame data on the basis of the result of estimation (step S150). Specifically, the processing circuit 110 calculates the amount of tissue displacement due to body motion or the like between the frames from the reception signals containing data sequences of the frames. The processing circuit 110 corrects the amount of displacement by moving the reception signals so that the positions thereof are aligned within the frame for which an integration process to be described later is performed with the use of the calculated amount of displacement. Here, a reference frame for calculating the amount of displacement may be just one frame for the entire data sequences, the reference frame may be changed according to the position in the time direction (that is, a plurality of reference frames may be provided), or the previous frame in the adjacent frames may be used as the reference frame. The reference frame may be selected arbitrarily from the data sequences, and for example, any of the first frame, the middle frame, or the last frame may be used as the reference frame.

The processing circuit 110 applies an MTI filter to the pieces of frame data with the amount of displacement corrected. This reduces the information derived from tissue that is stationary or has little movement between the frames (tissue signal component (clutter)), and extracts the blood flow-derived information (blood flow signal component) (step S170).

The acquisition function 111 adds up the pieces of frame data 20 and acquires the single addition data obtained thereby as first ultrasonic data 21 (step S200) as illustrated in FIG. 4. In other words, the acquisition function 111 acquires the first ultrasonic data 21 obtained based on the result of the ultrasonic scan of the subject. The first ultrasonic data 21 has a higher signal-noise (SN) ratio than each piece of frame data 20 before the addition. The first ultrasonic data 21 is blood flow data (power signal data) in which the blood flow-derived information is extracted. As illustrated in FIG. 5, in the method of generating the high-resolution data according to the conventional art, the addition process expressed at step S200 is not performed and the blood flow data 31 corresponding to each of the pieces of frame data 30 is generated.

The extraction function 112 performs a process of continuously extracting the signal components representing the object from the first ultrasonic data 21 (step S300). The object here is the object whose resolution is increased, and includes, for example, at least one of blood, an in-body tissue, or a contract agent. Continuously extracting the signal components representing the object means extracting the positions of signals (pixels) representing the object without a predetermined interval in the signal space or image space. For example, if the object is blood, the extraction function 112 extracts the positions of signals (pixels) representing blood without a predetermined interval in the signal space or image space. As a result, the extraction function 112 acquires a signal component 22, which is the extraction data representing the object, as illustrated in FIG. 4.

Figure 6:
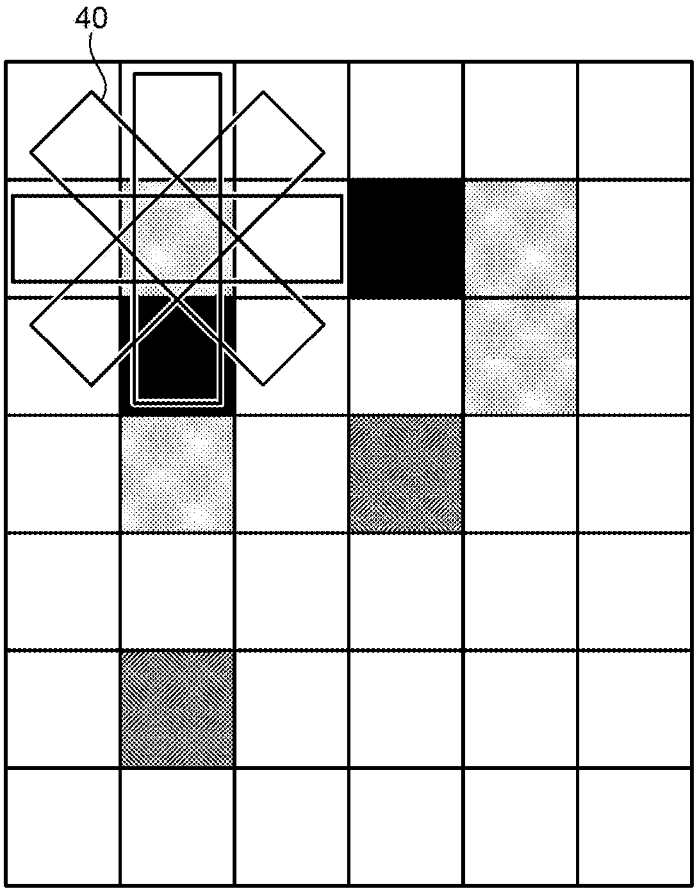
FIG. 6 is a diagram illustrating extraction of an object by a kernel according to the embodiment.

With reference to FIG. 6 and FIG. 7A to FIG. 7C, an example of a method for continuously extracting the signal components representing the object is described. For each of a plurality of attention positions included in the first ultrasonic data 21, based on a result of comparing a signal value at a position in predetermined attention direction and range with respect to the attention position and a signal value at the attention position, the extraction function 112 extracts a signal component at the attention position as the signal component representing the object. If the signal value at the attention position is more than or equal to the signal value at the position in the predetermined direction and range, the extraction function 112 extracts the signal component at the attention position as the signal component representing the object. The extraction function 112 extracts the position of signals (pixels) representing blood using a kernel 40 based on a ratio of 3 in height×1 in width, as illustrated in FIG. 6, for example. Here, for the convenience of description, the pixel value (luminance value) at the attention position and the pixel value at the position in the predetermined range are compared for each attention direction with respect to the attention position on the two-dimensional image in this example; however, the signal value at the attention position and the signal value at the position in the predetermined range may be compared one-dimensionally with respect to the first ultrasonic data 21. In other words, the signal components representing the object may be extracted without developing the first ultrasonic data 21 into an image.

Figures 7A, 7B:
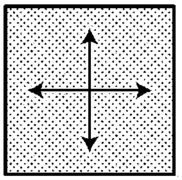
FIG. 7A is a diagram expressing a structure of first ultrasonic data.
FIG. 7B is a diagram expressing a result of extracting an object when a kernel according to the comparative example is used.

Each square cell in FIG. 7A represents each pixel value (luminance value) of the image represented by the first ultrasonic data 21. When extracting the positions with the relatively high pixel values from the first ultrasonic data 21, for example, as illustrated in FIG. 7B, a kernel with total of 9 cells of 3×3 cells are used, including the cell at the attention position and eight cells adjacent to that attention position. In this case, when the pixel value at the attention position is higher than that of any of the eight adjacent cells, the processing circuit 110 extracts the attention position as the position of the pixel (signal) representing blood.

Figure 7C:
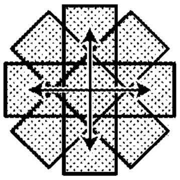
FIG. 7C is a diagram expressing a result of extracting the object when the kernel according to the embodiment is used.

However, when the kernel illustrated in FIG. 7B is used, the object (blood vessel or the like) is extracted discretely and its structure is not adequately represented. On the other hand, if the kernel 40 illustrated in FIG. 6 is used, the object is extracted continuously as illustrated in FIG. 7C. Specifically, the kernel 40 includes three cells in a row, each cell corresponding to a single pixel. The pixel corresponding to the central cell is the attention position, and the pixels corresponding to the two cells adjacent to the central cell are the positions to be compared. More specifically, when the kernel 40 is set at the position illustrated in FIG. 6, the pixel value at the attention position is higher than the pixel values at the adjacent positions, and therefore, that attention position is extracted as the object.

In the above example of the kernel 40, the signal components representing the object are extracted in four directions of vertical, horizontal, diagonally upper right, and diagonally upper left directions, but the shape and size of the kernel are not limited to this example. Even when the pixel value at the attention position is equal to the pixel value at the position in the predetermined direction and range, the extraction function 112 may extract the attention position as the object.

In other words, since the signal components representing the object can be continuously extracted from the first ultrasonic data 21 in the embodiment, the condition for extracting the signal components representing the object is looser than that in the conventional method. The extraction condition can be made loose because the data with a high SN ratio (the first ultrasonic data 21) obtained by the addition process at step S200 is targeted for extraction.

In the above example, the object is extracted pixel by pixel, but the object may be continuously extracted in groups with a plurality of pixels. When the object is extracted in groups with the pixels, the average or integrated value of the pixels constituting the group may be used as the pixel value (signal value) of that group. In this case, the extraction function 112 extracts, for each group having the pixels, the signal component representing the object on the basis of the result of comparing the pixel values of another group at the position in the predetermined direction and range with the pixel values of the group at the attention position.

In another example, for each of the attention positions included in the first ultrasonic data 29, the extraction function 112 may compare the signal value (pixel value) at the attention position and the signal value (pixel value) at the position in the predetermined range for each attention direction with respect to the attention position, and based on the result of the comparison and a weight coefficient determined in advance for each attention direction, may weight the signal component at the attention position. For example, in the case where the four directions of vertical, horizontal, diagonally upper right, and diagonally lower left directions are the attention directions, the weight coefficient is set in advance for each direction. If the pixel values at the attention positions in three directions of vertical, horizontal, and diagonally upper right directions are more than or equal to the adjacent pixel values, the extraction function 112 weights the pixel value at the attention position by the weight coefficient determined for each of the three directions (weight coefficient is multiplied by pixel value). As a result, the pixel value at the attention position is changed and emphasized based on the result of such comparison and the weight coefficient determined for each direction.

Subsequently, the output function 113 performs a process of outputting second ultrasonic data 23 on the basis of the continuously extracted signal components 22 (extraction data) representing the object at step S300 (step S400). For example, the output function 113 outputs synthesis data or correction data as the second ultrasonic data 23. As illustrated in FIG. 4, the synthesis data is obtained by synthesizing (adding) the continuously extracted signal components 22 (extraction data) representing the object and the first ultrasonic data 21 (power signal data). The correction data is obtained by correcting the first ultrasonic data 21 (power signal data) on the basis of the continuously extracted signal components 22 (extraction data) representing the object. The first ultrasonic data 29, which is the high-resolution image illustrated in FIG. 4, is an image formed by the second ultrasonic data 23 by the output function 113.

Figure 8:
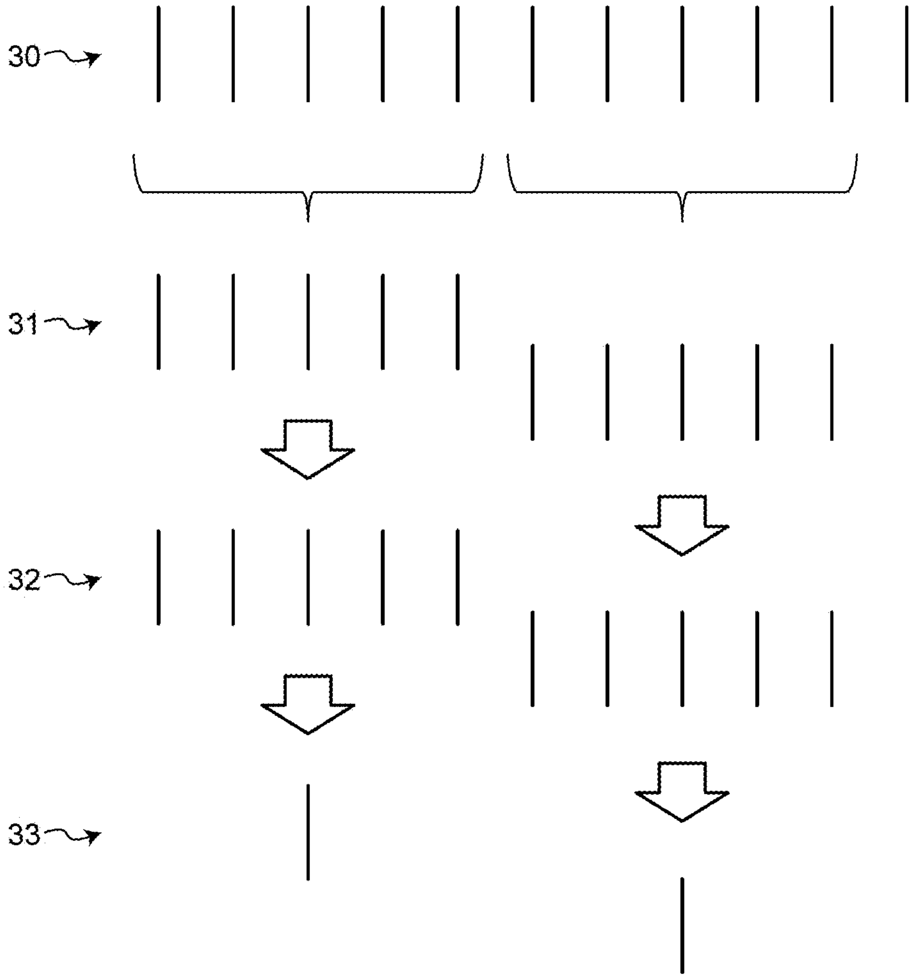
FIG. 8 is a diagram for describing signal processing according to the comparative example.
Figure 9:
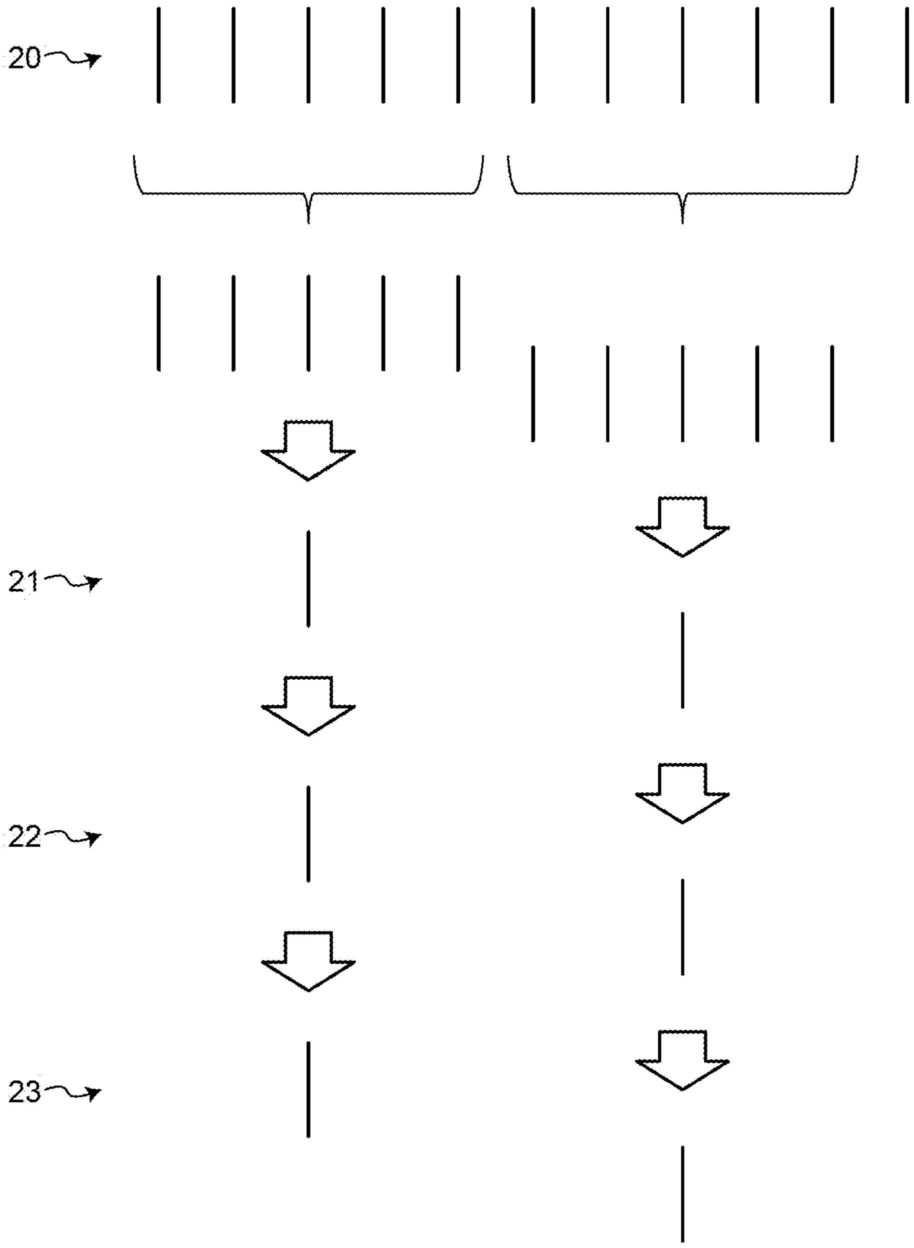
FIG. 9 is a diagram for describing signal processing according to the embodiment.

Next, with reference to FIG. 8 and FIG. 9, the signal processing in a comparative example and the signal processing in the embodiment are compared. As illustrated in FIG. 8, in the comparative example, the addition process according to this embodiment is not performed for the frame data 30, which includes about several thousand to several tens of thousands of pieces, and the pieces of blood flow data 31 (power signal data) corresponding to the frame data 30 are generated. In the comparative example, a high-luminance, spatially sparse signal with a large signal value (amplitude value) is extracted from each piece of blood flow data 31, and thus, extraction data 32 with a plurality of frames is obtained. In the comparative example, the extracted pieces of extraction data 32 are then integrated. As described above, in this method, if the number of frames used to extract the object is small, the object is extracted discretely (discontinuously) and the high-resolution blood flow data cannot be obtained. On the other hand, using more frames increases the load on the arithmetic processing, resulting in poor responsiveness.

Meanwhile, as illustrated in FIG. 9, in the medical information processing device 100 according to the embodiment, the acquisition function 111 adds up about several dozen to several hundreds of pieces of frame data 20 and acquires the single addition data obtained thereby as the first ultrasonic data 21. In the medical information processing device 100, the extraction function 112 performs a process of continuously extracting the signal components representing the object from the first ultrasonic data 21 to acquire the signal components 22 corresponding to the extraction data representing the object. The medical information processing device 100 then causes the output function 113 to output the second ultrasonic data 23 on the basis of the continuously extracted signal components representing the object. By this method, the object can be extracted continuously even if the number of frames used to extract the object is small. Thus, highly responsive and high-resolution ultrasonic data (high-resolution data) can be obtained. Moreover, by the ultrasonic diagnosis device according to this embodiment, the process of extracting the signal components representing the object can be reduced to 1/frame number, which can significantly reduce the arithmetic load compared to the conventional device.

Figure 10A:
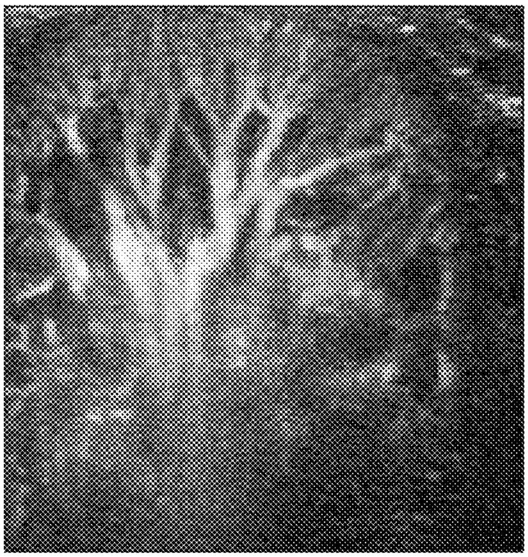
FIG. 10A is a diagram expressing ultrasonic data according to a first comparative example.
Figure 10B:
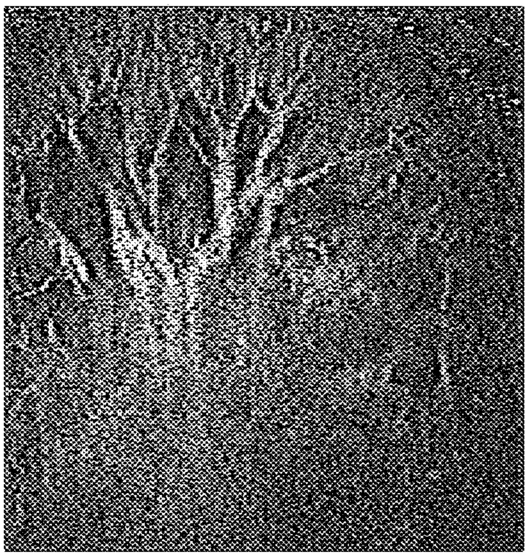
FIG. 10B is a diagram expressing ultrasonic data according to a second comparative example.
Figure 10C:
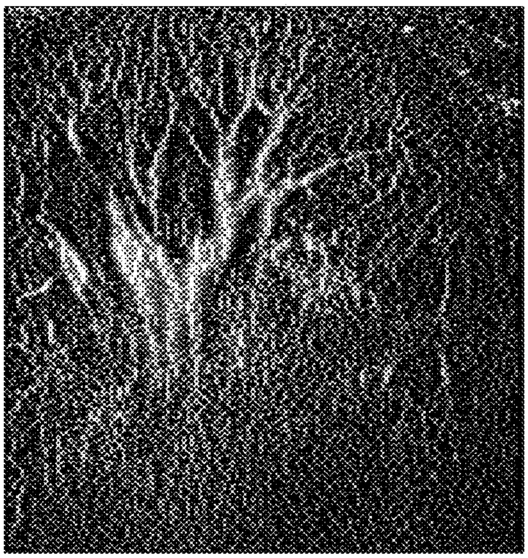
FIG. 10C is a diagram expressing second ultrasonic data (high-resolution image data) according to the embodiment.

With reference to FIG. 10A to FIG. 10C, the blood flow data in the comparative examples and the blood flow data in the embodiment are compared. FIG. 10A is an ultrasonic image (blood flow data) in a first comparative example, which is obtained using a superb micro-vascular imaging (SMI) method. FIG. 10B is an ultrasonic image (blood flow data) in a second comparative example, which is obtained by the conventional method illustrated in FIG. 5. FIG. 10C expresses the first ultrasonic data 29, which is a high-resolution image obtained by the method according to the embodiment expressed in FIG. 4. The high-resolution image 29 depicts blood flow in higher resolution than that of the ultrasonic image expressed in FIG. 10A. The high-resolution image 29 expressed in FIG. 10C depicts peripheral blood flow in more detail and with more continuity than the ultrasonic image expressed in FIG. 10B.

As described above, by the medical information processing device 100 according to the embodiment, the object (blood, contract agent, etc.) can be extracted continuously even if the number of frames used for object extraction is small. Thus, highly responsive and high-resolution ultrasonic data (high-resolution data) can be obtained. Moreover, by the ultrasonic diagnosis device according to this embodiment, the process of extracting the signal components representing the object can be reduced to 1/frame number, which can significantly reduce the arithmetic load compared to the conventional device.

Note that the embodiment is not limited by the above examples, and various changes can be made without departing from the gist thereof.

For example, in the above embodiment, the acquisition function 111 acquires, as the first ultrasonic data, the single addition data whose SN ratio is improved by adding up the pieces of frame data; however, the acquisition function 111 may alternatively acquire ultrasonic data whose SN ratio is improved without this addition process. For example, the acquisition function 111 may input the pieces of frame data 20 that are obtained by the ultrasonic scan of the subject and that are continuous in the time direction to a trained model that, upon input of the pieces of frame data that are obtained by the ultrasonic scan and that are continuous in the time direction, outputs a single piece of ultrasonic data with a higher SN ratio than that of the input frame data, and acquire the single ultrasonic data output from the trained data, as the first ultrasonic data 21. This trained model is trained by a dataset in which the pieces of frame data are the input data and the single ultrasonic data with a higher SN ratio than that of each piece of frame data is the teacher data. The acquisition function 111 inputs the pieces of frame data 20 to the trained model and acquires a single piece of ultrasonic data that is output from the trained model and that has a higher SN ratio than the pieces of frame data, as the first ultrasonic data 21.

The acquisition function 111 may omit the process of improving the SN ratio and may acquire the first ultrasonic data 21 obtained based on the result of the ultrasonic scan of the subject. For example, the acquisition function 111 may acquire the ultrasonic data with a high SN ratio received from an external workstation or the like as the first ultrasonic data 21.

In the above embodiment, the extraction function 112 performs the process of continuously extracting the signal components representing the object from the first ultrasonic data 21 by the kernel 40 illustrated in FIG. 6, for example, but may alternatively perform a process of extracting the signal components representing the object without using a kernel. For example, the extraction function 112 may input the first ultrasonic data 21 to the trained model that, upon input of a single piece of ultrasonic data with a higher SN ratio than those of the pieces of frame data that are obtained by the ultrasonic scan and that are continuous in the time direction, continuously outputs the signal components representing the object included in the ultrasonic data, and acquire the continuously extracted signal components 22 (extraction data) representing the object from the trained model. This trained model is trained by using, for example, a dataset in which the ultrasonic data with the improved SN ratio is the input data and the signal components that continuously represent the object in the ultrasonic data are the teacher data. The extraction function 112 inputs the first ultrasonic data acquired by the acquisition function 111 to the trained model and acquires the signal components that are output from the trained model and that continuously represent the object. Thus, the signal components representing the object can be continuously extracted from the first ultrasonic data 21 without using a kernel.

Figure 11:
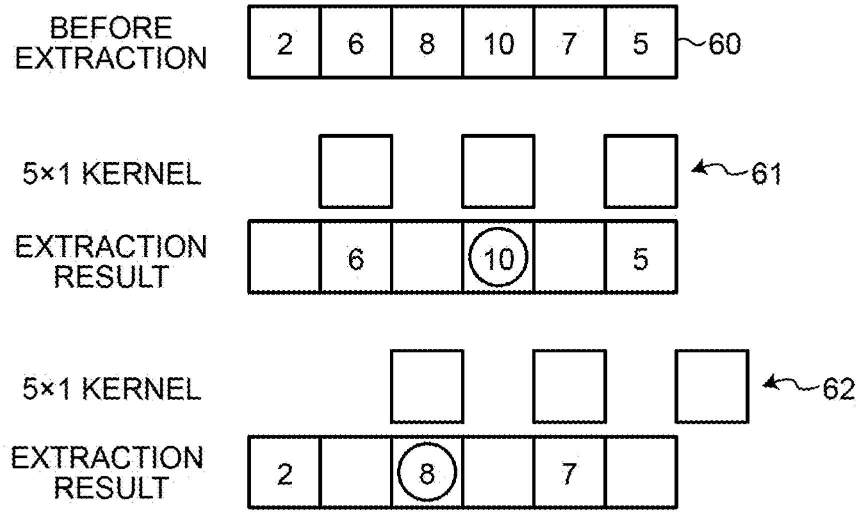
FIG. 11 is a diagram illustrating extraction of an object by a kernel according to another embodiment.

In the example described in the embodiment, the kernel is based on a ratio of 3 in height×1 in width; however, the kernel is not limited to this example. For example, as illustrated in FIG. 11, the kernel may be based on a ratio of, for example, 5 in height×1 in width, in which only the first, third, and fifth cells from the left among the 5×1 cells are used. For example, when a kernel 61 is applied to a pre-extraction signal 60, a signal value "10" is extracted. When a kernel 62 is applied to the pre-extraction signal 60 (when the kernel 61 is shifted by one cell to the right), a signal value "8" is extracted. Therefore, even in the case where a relatively large signal value exists adjacently in the direction where the kernel is disposed, the signal components representing the object (signal values "10" and "8") can be extracted continuously by using such kernels 61 and 62.

Although the high-resolution blood flow data is generated mainly in the example described above, the in-body tissue data or contrast data with high resolution can also be generated by the method according to the embodiment.

Second Embodiment

In the second embodiment, when output function 133 outputs the second ultrasonic data on the basis of the continuously extracted signal components representing the object at step S400, an improper signal point or an improper frame is specified from the continuously extracted signal components representing the object and based on the result of specifying the improper signal point or the improper frame, the second ultrasonic data is output. Japanese Patent Applications No. 2023-164256, filed on Sep. 27, 2023 is cited in the second embodiment and a modification of the second embodiment, for example.

Figure 12:
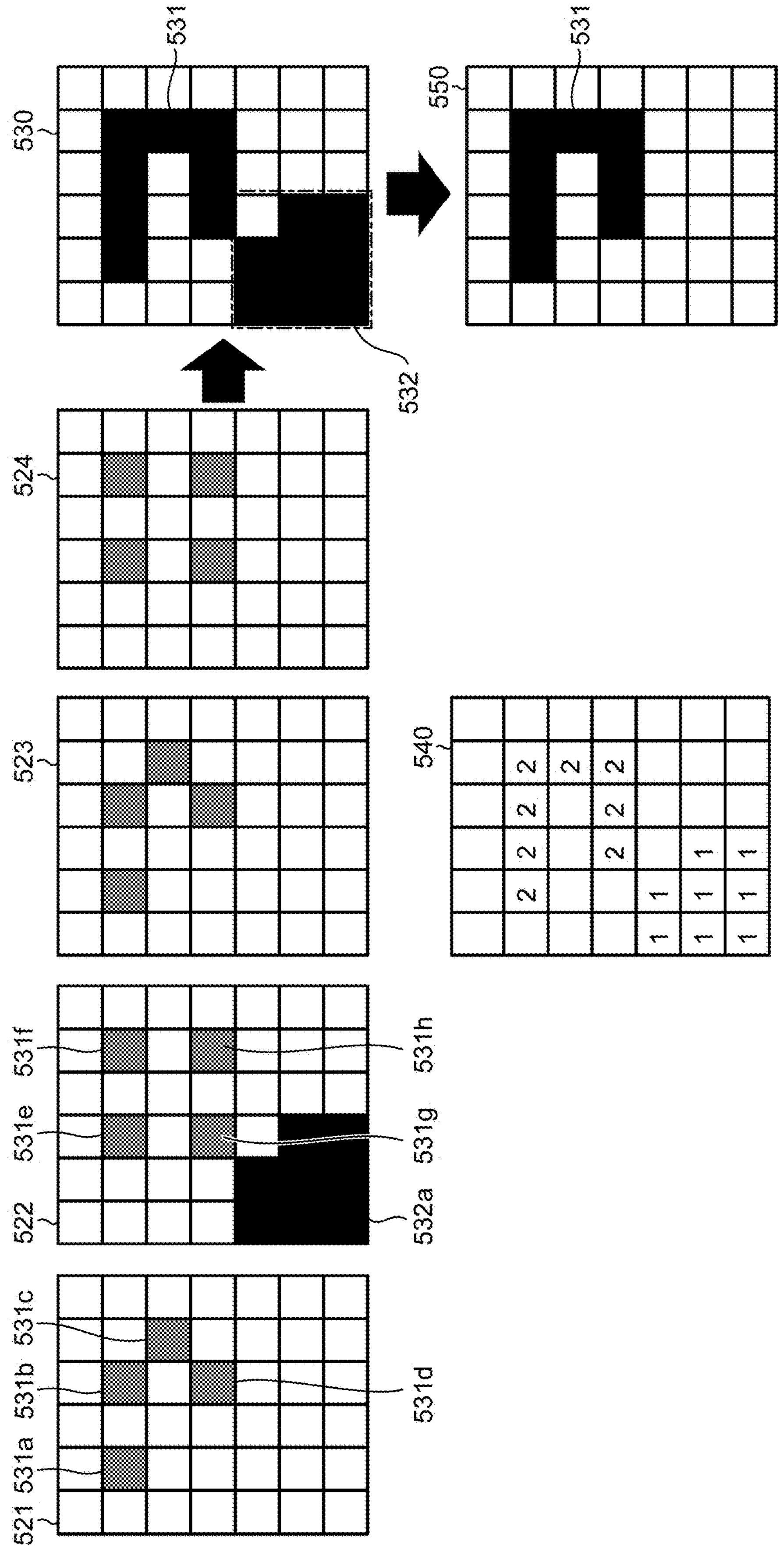
FIG. 12 is a diagram for describing a process according to a second embodiment.

FIG. 12 expresses a plurality of pieces of second signal data extracted at step S400. Here, frames 521 to 524 represent the respective frames of the first ultrasonic data in the frames, or the respective frames of the blood flow signal data for which the process at step S400 is performed for the first ultrasonic data in the frames and the clutter removal process is performed. For example, the data in the frame 521 represents the first signal data in the first frame or the blood flow signal data in the first frame after the clutter removal process is performed on the first signal data. The data in the frame 522 represents the first ultrasonic data in the second frame.

In the frames 521 to 524, the pixels drawn in gray or black represent the signal data extracted by the extraction function 112 at step S300. For example, in FIG. 12, points 531*a* to 531*d* are the signal data extracted as the second signal data in the frame 521, which is the first frame. In addition, points 531*e*, 531*f*, 531*g*, and 531*h* and a region 532*a* are the signal data extracted in the frame 522, which is the second frame. Among the frames 521 to 524, gray pixels represent signal points that are not extracted as improper signal points, and black pixels represent signal points that are extracted as improper signal points.

Subsequently, the output function 113 specifies the improper signal points from the signal data extracted at step S300. Here, the improper signal point is a signal point that is not considered to be the blood flow signal as the measurement target, such as clutter. Here, since it is considered that clutter and the like tend not to be extracted as high signal points across the frames at the same position, the output function 113 specifies the improper signal points on the basis of the signal extraction frequency across the frames. As an example, the output function 113 specifies the signal point at the position where the signal extraction frequency is less than the reference as the improper signal point.

For example, in FIG. 12, integrated signal data 530 expresses the second signal data after the integration process is performed in a process to be described later. The output function 113 generates a table 40 to count how many times each point has been extracted as a high signal point at each point. For example, the points 531*a*, 531*b*, 531*c*, etc. are extracted as the high signal points in two or more frames; therefore, the signal extraction frequency is “2”. On the other hand, the point that belongs to the region 532*a* is extracted as the high signal point only in the frame 522, which is the second frame, i.e., only in one frame; therefore, the signal extraction frequency is “1”.

Here, the processing circuit 110 sets the reference signal extraction frequency to “2”, for example. In that case, the output function 113 determines the signal points in the region 531, which are the signal points such as the points 531*a*, 531*b*, and 531*c* with a signal extraction frequency of 2 or more, to be the proper signal points. On the other hand, the output function 113 specifies the signal point in the region 532, where the signal extraction frequency is 1, as the improper signal point.

The output function 113 then integrates the second signal data in the frames extracted at step S300 to generate integrated signal data that combines the data in the respective frames. As an example, in FIG. 12, the output function 113 generates the integrated signal data 530 by integrating a plurality of pieces of second signal data that are the high signal points expressed in gray or black in the frames 521 to 524.

Subsequently, the output function 113 generates third signal data from which the improper signals are excluded, based on the result of specifying the improper signal points and the second signal data extracted at step S300. As an example, the output function 113 generates the third signal data by excluding the improper signal points from the integrated signal data 530, which results from the integration of the second signal data. In other words, the output function 113 generates the third signal data as the ultrasonic data by excluding the improper signal points from the integrated signal points. In one example, in FIG. 12, the output function 113 removes the signal point in the region 532, which is the signal point at the position where the signal point extraction frequency is less than the reference, from the integrated signal data 530 in which the second signal data is integrated, as the improper signal point from the integrated signal points, and generates third signal data 50 in which only the signal points in the proper region 531 are integrated.

As described above, in the second embodiment, the output function 113 generates the third signal data by specifying the improper signal points on the basis of the signal point extraction frequency. This allows the removal of signal points that are noise and therefore the image quality can be improved.

Modification of Second Embodiment

In the second embodiment, the processing circuit 110 specifies the improper signal points and excludes the specified improper signal points from the integrated signal points, thereby generating the third signal data. In a modification of the second embodiment, the third signal data is generated by specifying the improper frame instead of specifying the improper signal point.

In the modification of the second embodiment, the output function 113 specifies the improper frame from the second signal data extracted at step S300. Here, the improper frame is a frame estimated to include the signal point that is not considered to be the blood flow signal as the measurement target, such as clutter. Here, when viewed in the vicinity of the frame with the clutter in the frame direction, the number of extraction signals to be extracted as the high signal points is considered to suddenly change; therefore, the output function 113 specifies the improper frame on the basis of the number of extraction signals in the frame direction. As an example, the output function 113 specifies the frame for which the change in the number of extraction signals in the frame direction is larger than the reference as the improper frame.

Figure 13:
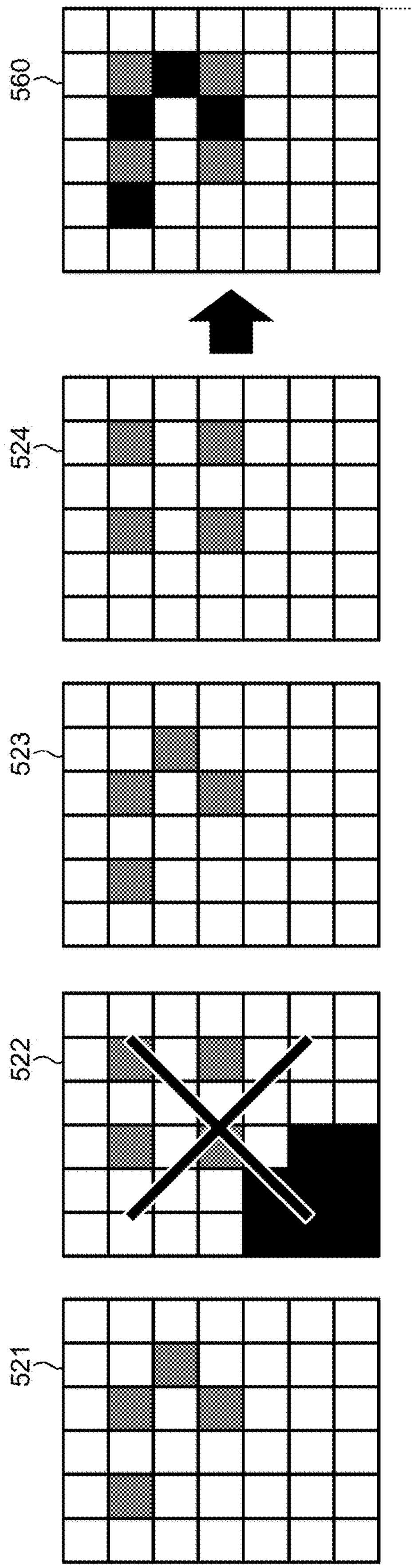
FIG. 13 is a diagram for describing a process according to a modification of the second embodiment.

For example, in FIG. 13, the frames 521 to 524 represent the respective frames among the first signal data in the frames. The signal points drawn in gray or black in the frames 521 to 524 represent the signal points with the high signal values extracted as the portions with the high signal values at step S300. Here, the output function 113 specifies the frame for which the change in the number of extraction signals in the frame direction is larger than the reference as the improper frame. In the example in FIG. 13, the number of signal points extracted as the signal points with the high signal values in the frame 522 is “12”. In the frames 521 and 523, the number of signal points extracted as the signal points with the high signal values is “4”. Thus, since the change in the number of extraction signals in the frame direction exceeds the reference in the vicinity of the frame 522, the output function 113 specifies the frame 522 as the improper frame.

The output function 113 generates the third signal data from which the improper frames are excluded, based on the result of specifying the improper frames and the second signal data specified at step S300. As an example, the output function 113 generates the third signal data by integrating the second signal data while excluding the improper frame from the integration target. As an example, in FIG. 13, the output function 113 generates third signal data 560 by integrating the second signal data while excluding the frame 522, which is the improper frame, from the integration target.

The above embodiment describes the case in which the processing circuit 110 extracts the improper frame on the basis of the change in the number of extraction signals in the frame direction, but the embodiment is not limited to this. The processing circuit 110 may specify the improper frame on the basis of the number of extraction signals itself in the frame direction. As an example, the processing circuit 110 may specify the frame in which the number of extraction signals in the frame direction is larger than the reference, as the improper frame.

As described above, in the modification of the second embodiment, the processing circuit 110 generates the third signal data by specifying the improper signal points on the basis of the signal point extraction frequency. This allows the removal of signal points that are noise and therefore the image quality can be improved.

Third Embodiment

In a third embodiment, the processes at step S300 and step S400 in the first embodiment are replaced by a different process. Specifically, in the third embodiment, the output function 113 divides the first ultrasonic data into a plurality of pieces of ultrasonic data, extracts a peak from each piece of ultrasonic data to extract the third ultrasonic data, assigns the third ultrasonic data to the corresponding position on the first ultrasonic data to generate fourth ultrasonic data, and combines the fourth ultrasonic data to generate the second ultrasonic data instead of step S300 and step S400 in the first embodiment. Japanese Patent Applications No. 2023-213406, filed on Dec. 18, 2023 is cited in the third embodiment, for example.

Figure 14:
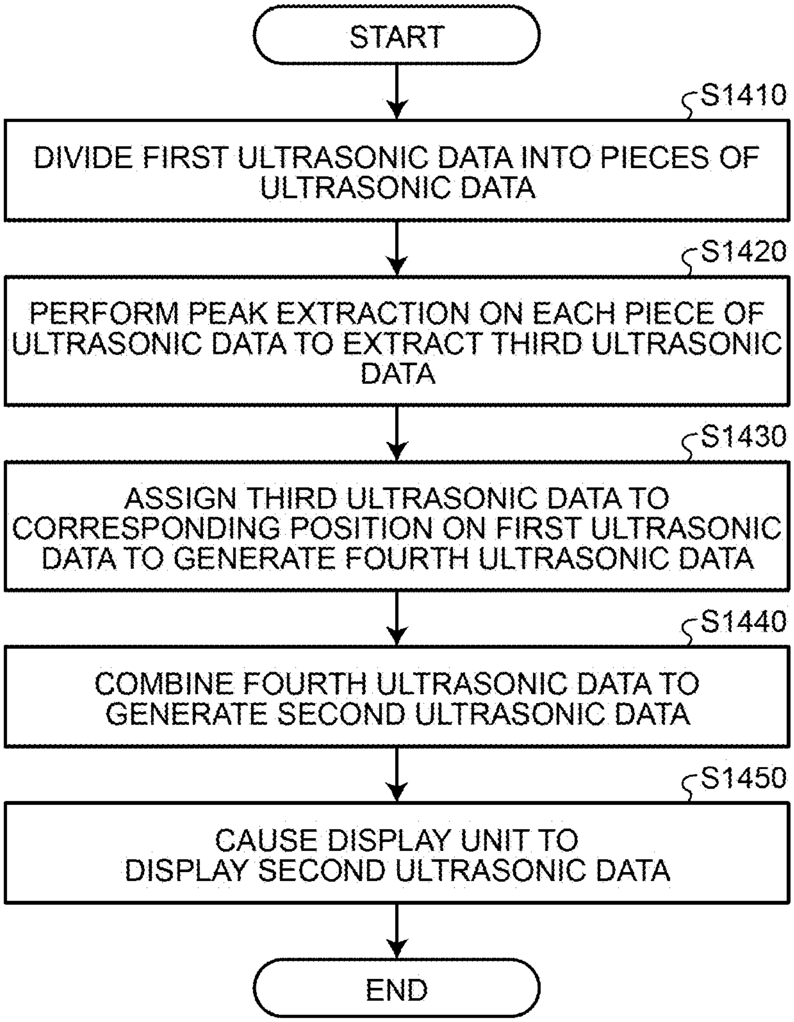
FIG. 14 is a flowchart expressing one example of a procedure of a process according to a third embodiment.
Figure 15:
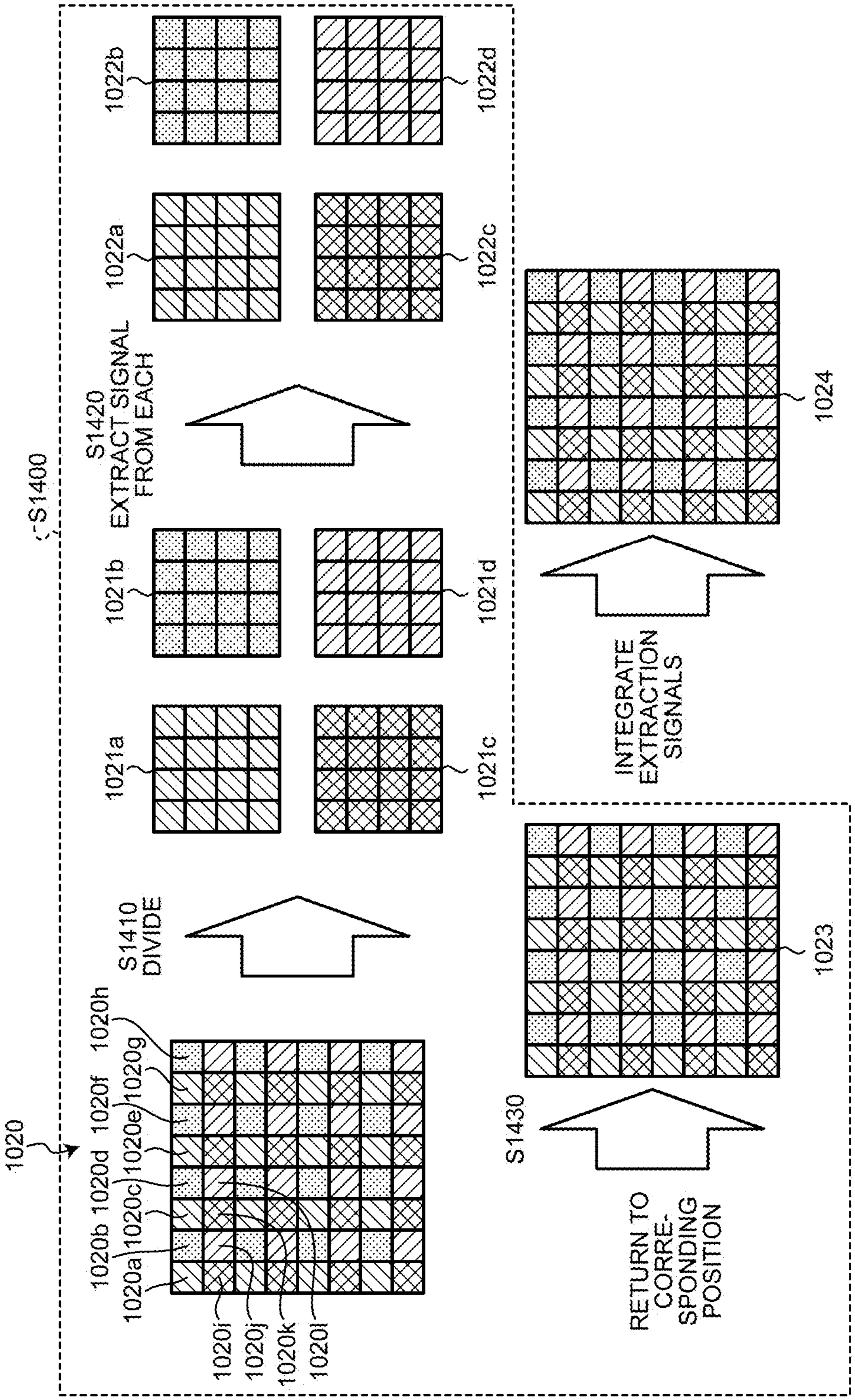
FIG. 15 is a diagram for describing an example of the process according to the third embodiment.

This process will be described with reference to FIG. 14 and FIG. 15. FIG. 14 is a diagram for more specifically describing a process performed in the third embodiment instead of steps S300 and S400 in FIG. 3. FIG. 15 is a diagram for describing a procedure of the process in FIG. 14.

In FIG. 15, image data 1020 represents the first ultrasonic data to be processed at step S400. Pixels 1020*a*, 1020*b*, 1020*c*, 1020*d*, 1020*e*, 1020*f*, 1020*g*, 1020*h*, 1020*i*, 1020*j*, 1020*k*, and 1020*l* represent the respective pixels in the image data 1020.

First, at step S1410, the output function 113 divides the first ultrasonic image data into a plurality of pieces of second ultrasonic image data. As an example, the output function 113 performs a data dividing process while thinning the data at equal intervals from the image data 1020, which is the first ultrasonic image data, so as to divide the data into four pieces of second ultrasonic image data. As an example, the output function 113 performs the data dividing process on every other piece of the image data 1020, which is the first ultrasonic image data, vertically and horizontally. For example, the output function 113 divides the data into image data 1021*a* including the pixels 1020*a*, 1020*c*, 1020*e*, 1020*g*, and the like, image data 1021*b* including the pixels 1020*b*, 1020*d*, 1020*f*, 1020*h*, and the like, image data 1021*c* including the pixels 1020*i*, 1020*k*, and the like, and image data 1021*d* including the pixels 1020*j*, 1020*l*, and the like in the drawing. In other words, the output function 113 performs the division of 2 in height×2 in width of the image data 1020, which is the first ultrasonic image data, into four pieces of ultrasonic data, that is, the image data 1021*a*, 1021*b*, 1021*c*, and 1021*d*.

In the aforementioned example, the output function 113 performs the division of 2 in height×2 in width of the image data 1020 into the four pieces of second ultrasonic image data; however, the embodiment is not limited to this. The output function 113 may perform the division of 3 in height×3 in width of the image data into nine pieces of ultrasonic data or may perform the division of 4 in height×4 in width of the image data into 16 pieces of ultrasonic data. Additionally, the embodiment is not limited to this, and the output function 113 may perform the division of 2×1 of the image data into two pieces of ultrasonic data only vertically or may perform the division of 1×2 of the image data into two pieces of ultrasonic data only horizontally.

Then, at step S1420, the output function 113 extracts the third ultrasonic data by extracting a peak from each piece of ultrasonic data.

As an example of the peak detection process at step S1420, the output function 113 extracts the high signal points using a kernel spreading over a total of nine signal points (3×3), including, for example, the attention point and the eight signal points adjacent to that attention point. In this case, the output function 113 extracts the attention point as the high signal point only if the attention point has a higher signal value than any of the signal points in the adjacent eight cells.

As another example of the peak detection process at step S1420, the output function 113 extracts the third ultrasonic data from the second ultrasonic data using a kernel extending in a particular direction, such as a kernel 4 with a size of 3×1.

As another example of the peak detection process at step S1420, the output function 113 extracts the third ultrasonic data from the second ultrasonic data using a trained model with machine learning.

In this way, the output function 113 extracts image data 1022*a*, 1022*b*, 1022*c*, and 1022*d*, which are the third ultrasonic data, from the image data 1021*a*, 1021*b*, 1021*c*, and 1021*d*, which are the second ultrasonic data, respectively.

Then, at step S1430, the output function 113 assigns the third ultrasonic data to the corresponding position on the first ultrasonic data to generate the fourth ultrasonic data. In other words, the output function 113 assigns the image data 1022*a*, 1022*b*, 1022*c*, and 1022*d*, which are the third ultrasonic data, to the corresponding positions on the first ultrasonic data to generate image data 1023, which is the fourth ultrasonic data.

Then, at step S1440, the output function 113 combines the fourth ultrasonic image data to generate the second ultrasonic data. Subsequently, at step S1450, the output function 113 outputs the second ultrasonic data.

Thus, in the third embodiment, the output function 113 applies the extraction process described above to each frame. In other words, the output function 113 extracts the second ultrasonic data by applying the kernel that extracts the high signal point to each of the frames. The processing circuit 110 adds up the second ultrasonic data in the respective frames as needed to generate image data 1024 to be output. Using the method according to the third embodiment makes it possible to extract the signal region with high luminance in a wider range.

Other Embodiments

The extraction of the local peak position in the first to third embodiments, etc., is not limited to the methods described above, and may be performed by other methods. For example, the local peak position may be extracted by peak sharpening with a nonlinear function applied to the signal values in the frame. In such a case, for example, an extraction function 110*g* first performs resampling on the first ultrasonic image data to increase the pixel density so as to increase the effective resolution. Here, resampling may, for example, replace each pixel with smaller pixels. The signal value of each pixel after the replacement may be interpolated from the original signal value (signal value before replacement) by, for example, bicubic interpolation.

Furthermore, the extraction function 110*g* sharpens the local peak by exponentiating each signal value of the first ultrasonic data after the resampling (for example, by 8th power, 12th power, etc.). The extraction function 110*g* extracts the local peak position by performing, for example, a thresholding process on the signal values after exponentiation. In other words, the extraction function 110*g* extracts identification information that represents the position extracted as the local peak as "1" and the position not extracted as the local peak as "0". The extraction function 110*g* extracts identification information from each piece of the first ultrasonic data by performing the above-described local peak sharpening process on the pieces of first ultrasonic data. The object of the local peak sharpening process described above is not limited to the first ultrasonic data and may alternatively be the frame data.

The above-mentioned embodiments may be combined with each other as appropriate.

With respect to the above embodiments, the following notes are disclosed as some aspects and selective features of the invention.

Note 1

The ultrasonic diagnosis device 10 as the medical information processing device provided in one aspect of the present invention includes the processing circuit 110. The processing circuit 110 causes the acquisition function 111 to acquire the first ultrasonic data 21 obtained based on the result of the ultrasonic scan of the subject. The processing circuit 110 causes the extraction function 112 to continuously extract the signal components 22 representing the object from the first ultrasonic data 21. The processing circuit 110 causes the output function 113 to output the second ultrasonic data 23 on the basis of the continuously extracted signal components 22 representing the object.

Note 2

The processing circuit 110 may cause the acquisition function 111 to acquire, as the first ultrasonic data 21, the addition data obtained by collecting the pieces of frame data 20 that are obtained by the ultrasonic scan and that are continuous in the time direction and adding up the pieces of frame data 20.

Note 3

The processing circuit 110 may cause the output function 113 to output, as the second ultrasonic data 23, the synthesis data obtained by synthesizing the continuously extracted signal components 22 representing the object and the first ultrasonic data 21.

Note 4

The processing circuit 110 may cause the output function 113 to output, as the second ultrasonic data 23, the correction data obtained by correcting the first ultrasonic data 21, based on the continuously extracted signal components 22 representing the object.

Note 5

The processing circuit 110 may cause the extraction function 112 to, for each of the attention positions included in the first ultrasonic data 21, extract the signal component at the attention position as the signal component 22 representing the object, based on the result of comparing the signal value at the position in the predetermined attention direction and range with respect to the attention position and the signal value at the attention position.

Note 6

The processing circuit 110 may cause the extraction function 112 to, when the signal value at the attention position is more than or equal to the signal value at the position in the predetermined direction and range, extract the signal component at the attention position as the signal component 22 representing the object.

Note 7

The processing circuit 110 may cause the extraction function 112 to, for each of the attention positions included in the first ultrasonic data 21, compare the signal value at the attention position and the signal value at the position in the predetermined range for each attention direction with respect to the attention position, and based on the result of the comparison and a weight coefficient determined in advance for each attention direction, weight the signal component at the attention position.

Note 8

The processing circuit 110 may cause the extraction function 112 to input the first ultrasonic data 21 to the trained model that, upon the input of a single piece of ultrasonic data with a higher SN ratio than the pieces of frame data that are obtained by the ultrasonic scan and that are continuous in the time direction, continuously outputs the signal components representing the object included in the ultrasonic data, and acquire the continuously extracted signal components 22 representing the object from the trained model.

Note 9

The object may include at least one of blood, an in-body tissue, and a contract agent.

Note 10

The ultrasonic diagnosis device 10 provided in one aspect of the present invention includes an execution unit that causes the ultrasonic probe 5 to perform the ultrasonic scan, and the processing circuit 110. The processing circuit 110 causes the acquisition function 111 to acquire the first ultrasonic data 21 obtained based on the result of the ultrasonic scan of the subject. The processing circuit 110 causes the extraction function 112 to continuously extract the signal components 22 representing the object from the first ultrasonic data 21. The processing circuit 110 causes the output function 113 to output the second ultrasonic data 23 on the basis of the continuously extracted signal components 22 representing the object.

Note 11

A computer program provided in one aspect of the present invention causes a computer to perform a process including: acquiring the first ultrasonic data 21 obtained based on the result of the ultrasonic scan of the subject; extracting continuously the signal components 22 representing the object from the first ultrasonic data 21; and outputting the second ultrasonic data 23, based on the continuously extracted signal components 22 representing the object.

According to at least one embodiment described above, the ultrasonic data with high responsiveness and high resolution can be obtained.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing device, comprising:
a processing circuit configured to:
perform an ultrasonic scan of a subject;
acquire addition data as first ultrasonic data by adding up a plurality of pieces of frame data that are continuous in a time direction and that are obtained based on a result of the ultrasonic scan of the subject, the addition data having a higher signal-noise (SN) ratio than each of the plurality of pieces of frame data;
acquire a signal component representing a spatially continuous object by extracting a local peak position from the first ultrasonic data; and
output second ultrasonic data, based on the acquired signal component representing the spatially continuous object.

2. The medical information processing device according to claim 1, wherein the processing circuit is further configured to output, as the second ultrasonic data, synthesis data obtained by synthesizing the first ultrasonic data and the acquired signal component representing the spatially continuous object.

3. The medical information processing device according to claim 1, wherein the processing circuit is further configured to output, as the second ultrasonic data, correction data obtained by correcting the first ultrasonic data, based on the acquired signal component representing the spatially continuous object.

4. The medical information processing device according to claim 1, wherein the processing circuit is further configured to, for each of a plurality of attention positions included in the first ultrasonic data, extract a signal component at the attention position as the signal component representing the spatially continuous object, based on a result of comparing a signal value at a position in a predetermined attention direction and range with respect to the attention position and a signal value at the attention position.

5. The medical information processing device according to claim 4, wherein the processing circuit is further configured to, when the signal value at the attention position is more than or equal to the signal value at the position in the predetermined direction and range, extract the signal component at the attention position as the signal component representing the spatially continuous object.

6. A medical information processing device, comprising:
a processing circuit configured to:
acquire first ultrasonic data obtained based on a result of an ultrasonic scan of a subject;
extract continuously a signal component representing an object from the first ultrasonic data; and
output second ultrasonic data, based on the continuously extracted signal component representing the object, wherein the processing circuit is further configured to, for each of a plurality of attention positions included in the first ultrasonic data, extract a signal component at the attention position as the signal component representing the object, based on a result of comparing a signal value at a position in predetermined attention direction and range with respect to the attention position and a signal value at the attention position,
wherein the processing circuit is further configured to, for each of the attention positions included in the first ultrasonic data, compare the signal value at the attention position and the signal value at the position in the predetermined range for each attention direction with respect to the attention position, and based on a result of the comparison and a weight coefficient determined in advance for each attention direction, weight the signal component at the attention position.

7. The medical information processing device according to claim 1, wherein the processing circuit is further configured to acquire the addition data as the first ultrasonic data by using a trained model and adding up the plurality of pieces of frame data that are continuous in the time direction, the addition data having a higher signal-noise (SN) ratio than each of the plurality of pieces of frame data.

8. The medical information processing device according to claim 1, wherein the processing circuit is further configured to acquire the signal component representing the spatially continuous object by using a trained model and extracting the local peak position from the first ultrasonic data.

9. The medical information processing device according to claim 1, wherein the spatially continuous object includes at least one of blood, an in-body tissue, and a contrast agent.

10. The medical information processing device according to claim 1, wherein the processing circuit is further configured to specify an improper signal point or an improper frame from the acquired signal component representing the spatially continuous object, and based on a result of specifying the improper signal point or the improper frame, output the second ultrasonic data.

11. The medical information processing device according to claim 10, wherein the processing circuit is further configured to generate the second ultrasonic data by excluding the improper signal point from the signal point after integration.

12. The medical information processing device according to claim 10, wherein the processing circuit is further configured to specify a signal point at a position where a signal extraction frequency is less than a reference, as the improper signal point.

13. The medical information processing device according to claim 10, wherein the processing circuit is further configured to specify a frame in which a change in number of extraction signals in a frame direction is more than a reference, as the improper frame.

14. The medical information processing device according to claim 1, wherein the processing circuit is further configured to:
divide the first ultrasonic data into a plurality of pieces of ultrasonic data, extract a peak from each of the pieces of ultrasonic data, and extract third ultrasonic data,
assign the third ultrasonic data to a corresponding position on the first ultrasonic data and generate fourth ultrasonic data, and
combine the fourth ultrasonic data and generate the second ultrasonic data.

15. An ultrasonic diagnosis device, comprising:
a transmitter/receiver circuit configured to cause an ultrasonic probe to perform an ultrasonic scan of a subject; and
a processing circuit configured to:
acquire addition data as first ultrasonic data by adding up a plurality of pieces of frame data that are continuous in a time direction and that are obtained based on a result of the ultrasonic scan of the subject, the addition data having a higher signal-noise (SN) ratio than each of the plurality of pieces of frame data;

acquire a signal component representing a spatially continuous object by extracting a local peak position from the first ultrasonic data; and output second ultrasonic data, based on the acquired signal component representing the spatially continuous object.

16. A medical information processing method, comprising:

performing an ultrasonic scan of a subject;

acquiring addition data as first ultrasonic data by adding up a plurality of pieces of frame data that are continuous in a time direction and that are obtained based on a result of the ultrasonic scan of the subject, the addition data having a higher signal-noise (SN) ratio than each of the plurality of pieces of frame data;

acquiring a signal component representing a spatially continuous object by extracting a local peak position from the first ultrasonic data; and outputting second ultrasonic data, based on the continuously-extracted acquired signal component representing the spatially continuous object.

* * * * *